US011911265B2

(12) United States Patent
Limsakoune et al.

(10) Patent No.: US 11,911,265 B2
(45) Date of Patent: Feb. 27, 2024

(54) AUTOMATED HEART VALVE SEWING

(71) Applicant: Edwards Lifesciences Corporation, Irvine, CA (US)

(72) Inventors: Chacphet Limsakoune, Corona, CA (US); Nina Robson, Fullerton, CA (US); Jeanette Jasmine Corona, Anaheim, CA (US); Michael R. White, Orange, CA (US); Juan Cuevas, Fullerton, CA (US); David Estelle, Azusa, CA (US); Michael Mashni, Yorba Linda, CA (US); Oscar Rosales, Buena Park, CA (US); Mitchell Salgado, Fullerton, CA (US); Kenny Yin, Fullerton, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 238 days.

(21) Appl. No.: 16/938,879

(22) PCT Filed: Jan. 11, 2019

(86) PCT No.: PCT/US2019/013340
§ 371 (c)(1),
(2) Date: Jul. 24, 2020

(87) PCT Pub. No.: WO2019/140293
PCT Pub. Date: Jul. 18, 2019

(65) Prior Publication Data
US 2021/0000591 A1    Jan. 7, 2021

Related U.S. Application Data

(60) Provisional application No. 62/617,114, filed on Jan. 12, 2018.

(51) Int. Cl.
*A61F 2/24* (2006.01)

(52) U.S. Cl.
CPC .... *A61F 2/2415* (2013.01); *A61F 2220/0075* (2013.01); *A61F 2240/001* (2013.01)

(58) Field of Classification Search
CPC ............ A61F 2/2415; A61F 2220/0075; A61F 2240/001; A61F 2/2412; D05B 23/00
(Continued)

(56) References Cited

U.S. PATENT DOCUMENTS 2,655,885 A * 10/1953 Dabrowski ............ D05B 35/00
112/231
3,347,190 A    10/1967 Roth
(Continued)

FOREIGN PATENT DOCUMENTS

CN    101506424 A    8/2009
EP    0794277 A1    9/1997
(Continued)

*Primary Examiner* — Suzette J Gherbi
(74) *Attorney, Agent, or Firm* — Chang & Hale LLP

(57) ABSTRACT

A system that can be used for suturing implants includes a first automated fixture that can comprise an articulation arm and a target device holder and a second automated fixture configured to operate as a sewing machine to sew material onto the implant. The second automated fixture uses a curved needle to form a stitch without having to release the needle in the process. The second automated fixture can also include a stitch looper that moves in coordination with the curved needle to perform a single-suture or single-thread stitch.

19 Claims, 14 Drawing Sheets

(58) Field of Classification Search
USPC .................................................. 623/2.1–2.18
See application file for complete search history.

(56) References Cited

U.S. PATENT DOCUMENTS

| | | | |
|---|---|---|---|
| 4,205,616 A | 6/1980 | Sugahara | |
| 4,692,164 A | 9/1987 | Dzemeshkevich et al. | |
| 5,095,833 A | 3/1992 | Darrieux | |
| 6,189,747 B1 | 2/2001 | Collingham et al. | |
| 6,295,940 B1 | 10/2001 | Shonteff | |
| 6,453,062 B1 | 9/2002 | MacNutt et al. | |
| 6,464,707 B1 * | 10/2002 | Bjerken | A61F 2/2415 606/139 |
| 7,739,971 B2 | 6/2010 | Chambers et al. | |
| 8,276,533 B2 | 10/2012 | Chambers et al. | |
| 8,695,518 B2 * | 4/2014 | Landoni | D05B 55/14 112/470.13 |
| 9,301,835 B2 | 4/2016 | Campbell et al. | |
| 9,339,378 B2 | 5/2016 | Quadri et al. | |
| 10,119,882 B2 | 11/2018 | Van Nest et al. | |
| 10,980,650 B2 * | 4/2021 | Cartledge | A61F 2/82 |
| 11,426,196 B2 * | 8/2022 | Rohl | A61B 90/00 |
| 2005/0013841 A1 | 1/2005 | Phillips et al. | |
| 2006/0070563 A1 | 4/2006 | Rawson | |
| 2006/0254485 A1 * | 11/2006 | Singh | D05B 15/00 112/80.55 |
| 2006/0276889 A1 * | 12/2006 | Chambers | A61F 2/2415 112/475.08 |
| 2008/0035038 A1 * | 2/2008 | Ekholm | D05B 19/16 112/2 |
| 2010/0192822 A1 * | 8/2010 | Landoni | D05B 19/12 112/117 |
| 2010/0257735 A1 | 10/2010 | Chambers et al. | |
| 2014/0033959 A1 | 2/2014 | Evans et al. | |
| 2014/0216317 A1 * | 8/2014 | Landoni | D05B 55/08 112/470.01 |
| 2017/0325976 A1 | 11/2017 | Nguyen et al. | |
| 2018/0250129 A1 | 9/2018 | Koral et al. | |
| 2020/0229917 A1 * | 7/2020 | Koral | D05B 19/16 |

FOREIGN PATENT DOCUMENTS

| | | |
|---|---|---|
| JP | H0666580 A | 3/1994 |
| JP | H09510900 A | 11/1997 |
| WO | 9527096 A1 | 10/1995 |
| WO | 9530387 A1 | 11/1995 |
| WO | 0182781 A2 | 11/2001 |
| WO | 2008016760 A2 | 2/2008 |
| WO | 2015070249 A1 | 5/2015 |
| WO | 2017188444 A1 | 11/2017 |
| WO | 2018156767 A1 | 8/2018 |
| WO | 2019140293 A1 | 7/2019 |

* cited by examiner

AUTOMATED HEART VALVE SEWING

RELATED APPLICATIONS

The present application claims priority under 35 U.S.C. § 371 to International Patent Application No. PCT/US2019/013340, filed Jan. 11, 2019, which claims priority to U.S. Provisional Patent Application Ser. No. 62/617,114 to Limsakoune et al., entitled "Automated Heart Valve Sewing", filed Jan. 12, 2018, both of which are incorporated herein by reference.

BACKGROUND

Medical devices, prosthetic implants, prosthetic heart valves, etc. can require sewing, treatment, inspection, etc. of certain portions and/or components thereof. Accuracy and/or efficiency in execution of suturing or other operations for such devices can be important. Furthermore, certain heart valve suturing operations or other operations can be time consuming and difficult.

SUMMARY

This summary is meant to provide some examples and is not intended to be limiting of the scope of the invention in any way. For example, any feature included in an example of this summary is not required by the claims, unless the claims explicitly recite the features. Also, the features, steps, concepts, etc. described in examples in this summary and elsewhere in this disclosure can be combined in a variety of ways. The description herein relates to devices, apparatuses, systems, assemblies, methods, combinations, etc. that can be utilized for manufacturing and processing heart valves and/or associated or related components, devices, apparatuses, etc. Among other features, these or elements of these can utilize or include logic that may receive a set of parameters as input that may be graphically displayed, and/or may be analyzed and new data generated and/or graphically displayed, to a user after the parameters have been received as input.

In some implementations, the present disclosure relates to a method of manufacturing a target device or component, for example, to a method of manufacturing, or suturing, a prosthetic implant device (e.g., a prosthetic human implant device, prosthetic heart valve, prosthetic human heart valve, etc.). The method comprises directing (e.g., providing input, programming, running a program, pushing a button, clicking an icon, etc. to cause) the automated fixture to position the target device (e.g., prosthetic implant device, etc.) in a first position, executing a first operation or procedure on the target device, directing (e.g., providing input, programming, running a program, pushing a button, clicking an icon, etc. to cause) the automated fixture to position the target device in a second position, and executing a second operation or procedure on the target device. The method can comprise disposing the target device on a holder component.

The method can also comprise using a needle and a stitch looper to form a stitch on the target device such that a stitch is formed without the needle releasing the suture or thread. The needle can be a curved needle that moves in a reciprocating fashion in conjunction with the stitch looper that moves in a reciprocating fashion in coordination with the curved needle to form the stitches on the target device.

In some implementations, a method of suturing an implant device comprises disposing the a target or implant device (e.g., a prosthetic heart valve, etc.) on a holder component of a first automated fixture and directing (e.g., providing input, programming, running a program, pushing a button, clicking an icon, etc. to cause) the first automated fixture to position the target or implant device in a first position.

In some implementations, the method also includes directing (e.g., providing input, programming, running a program, pushing a button, clicking an icon, etc. to cause) a second automated fixture to execute a first stitch on the implant device by passing a curved needle into and out of a material being sutured to the target or implant device.

The method can also comprise directing (e.g., providing input, programming, running a program, pushing a button, clicking an icon, etc. to cause) the first automated fixture to position the target or implant device in a second position (and, optionally, a third, fourth, fifth, and/or further additional positions).

In some embodiments, the method also includes directing (e.g., providing input, programming, running a program, pushing a button, clicking an icon, etc. to cause) the second automated fixture to execute a second stitch on the implant device by passing the curved needle into and out of the material being sutured to the target or implant device.

The second automated fixture can include a stitch looper that moves in coordination with the curved needle to form the first and second stitches.

The method can also comprise directing the first automated fixture to circumferentially rotate the implant device in place.

In some embodiments, the method comprises loading a pre-programmed suturing procedure script using one or more processors configured to control the first automated fixture and the second automated fixture.

The second automated fixture can use the curved needle to execute the first stitch such that the first stitch is a single suture stitch. The curved needle can be configured to pass into and out of the material along a fixed path of the curved needle. The curved needle can pass through the material at two different locations for each of the first stitch and the second stitch.

The stitch looper can include two or more tines to secure a portion of the suture as the curved needle is withdrawn through insertion points formed during formation of the first stitch. The stitch looper can be configured to rotate to form a loop with the portion of the suture to form the first stitch. The curved needle can pass through the loop formed by the stitch looper to form the first stitch.

In some implementations, a suturing system comprises one or more automated fixtures. For example, the system comprises at least a first automated fixture. The first automated fixture can comprise a plurality of motorized actuator devices and a suture target holder. The first automated fixture is configured to move or rotate a target suture device (e.g., a heart valve, etc.), for example, when the target suture device is mounted to the suture target holder.

In some embodiments, the system also includes at least a second automated fixture. In some embodiments, the second automated fixture comprises a curved needle and can be configured to move the curved needle in a fixed path.

In some embodiments, the second automated fixture also includes a stitch looper. The stitch looper can have one or a plurality of tines. The stitch looper (e.g., tines of the stitch looper) can be configured to secure a portion of a suture and to form a loop using the portion of the suture as the curved needle moves in the fixed path. In some embodiments, the stitch looper moves along a second fixed path that includes rotation of the stitch looper to form the loop using the portion of the suture. Movement of the curved needle can be locked or synchronized to movement of the stitch looper.

In some embodiments, the first automated fixture and the second automated fixture of the system are arranged relative to each other and configured such that the first automated fixture can move the target suture device in three dimensions to position the target suture device in the path of the curved needle. The system and component or fixtures thereof can be configured to implement a predetermined suturing pattern on the target suture device.

In some embodiments, the first automated fixture comprises a first controller configured to direct the first automated fixture how to position the target suture device. In some embodiments, the second automated fixture comprises a second controller configured to direct the second automated fixture when to move the curved needle to implement the suturing pattern.

The second automated fixture can include a tensioning device that can keep a suture in a state of constant tension when implementing the suturing pattern.

In some embodiments, the first automated fixture is configured to move the target suture device in at least four directions. The first automated fixture can comprise an articulation arm.

The system, e.g., the second automated fixture of the system, can be configured such that the curved needle is used to implement the suturing pattern as a single suture stitching.

Other steps, features, components, etc. not specifically mentioned in these examples, but described elsewhere herein or otherwise known can also be included and/or used with the examples described here.

BRIEF DESCRIPTION OF THE DRAWINGS

Various embodiments are depicted in the accompanying drawings for illustrative purposes and should in no way be interpreted as limiting the scope of any of the inventions disclosed herein. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
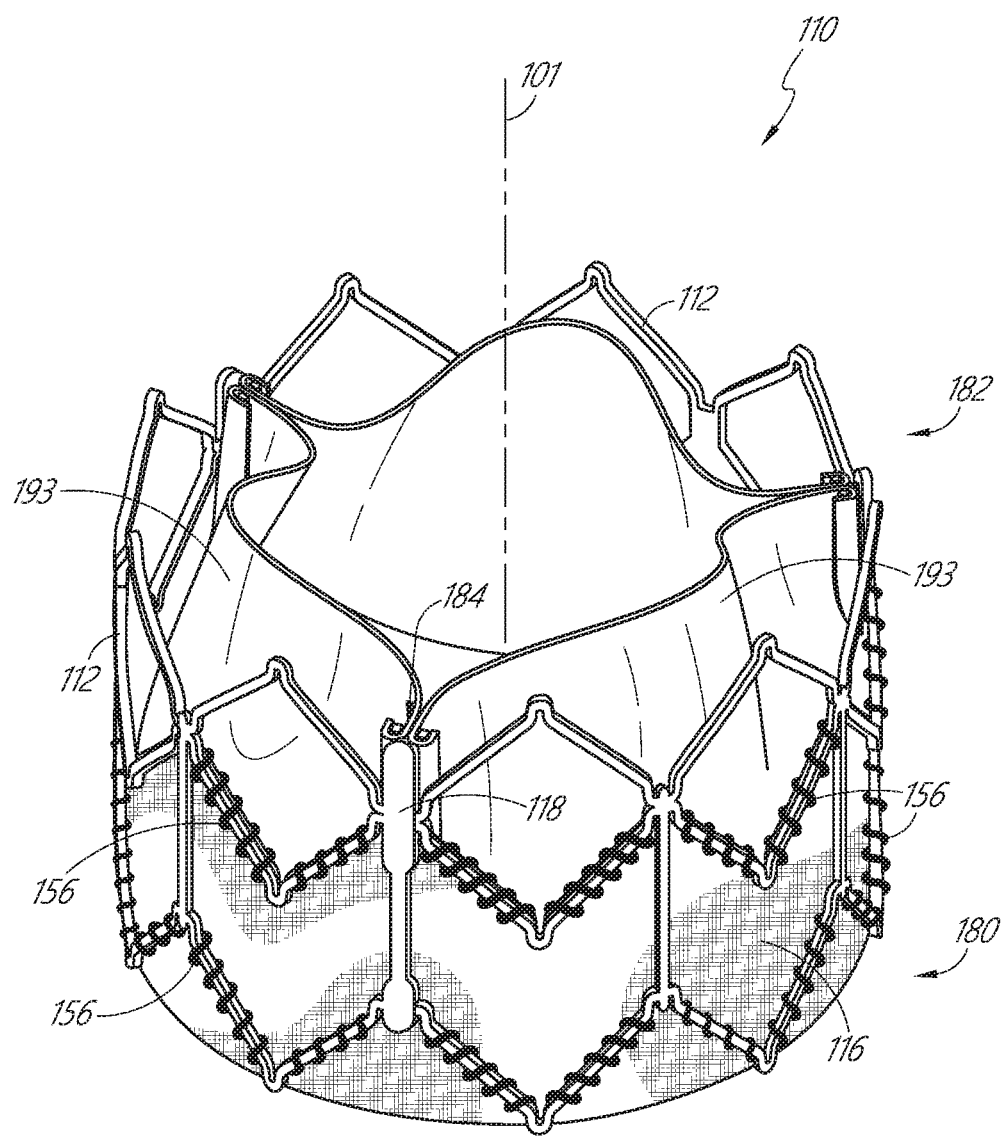
FIG. 1 illustrates an example of an implantable prosthetic valve device.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Further, one or more steps disclosed with respect to one method may be incorporated into other methods disclosed herein. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. Features described with respect to one exemplary embodiment may be incorporated into other embodiments disclosed herein even if not specifically described with respect to the embodiment.

Prosthetic heart valve implants, as well as many other types of prosthetic implant devices and other types of devices, can comprise various sutured components and/or portions. For example, a sealing portion, skirt, etc. can be sutured to a frame of a prosthetic heart valve to help prevent blood from leaking around the outer edges or circumference of the prosthetic heart valve. Execution of sutures by a human operator may be relatively difficult and/or cumbersome in certain conditions. For example, where small stitches are to be made with high precision, the complexity and/or associated operator burden may result in injury and/or undesirably low quality of products. Furthermore, certain heart valve implant devices may require hundreds of sutures, which can involve substantially labor-intensive and error-susceptible suturing procedures. Therefore, adding automation to suturing of implants can be desirable to improve quality, speed of manufacture, and/or help prevent issues associated with human operators.

Certain embodiments disclosed herein provide heart valve suturing systems, devices, and/or methods for performing suturing procedures involving the physical manipulation and/or positioning of one or more automated mechanical articulating fixtures, components and/or subassemblies. Such articulating fixture(s) or component(s) may be configured to hold or secure a prosthetic human heart valve implant device, or other suturing subject or implant device having one or more components or portions that may advantageously be sutured together. The various embodiments relating to heart valve suturing presented herein can be applicable to heart valves having any type of suturing and/or structural configuration or pattern. Examples of heart valve structures and heart valve suturing techniques that may be applicable to certain embodiments presented herein are disclosed in WIPO Publication No. WO 2015/070249, the entire contents of which are hereby expressly incorporated by reference.

FIG. 1 illustrates an implantable prosthetic human valve device 110 according to one or more embodiments. The features of valve 110 described herein can apply to other valves, including other valves described elsewhere herein. The valve 110 can be, for example, a transcatheter heart valve (THV), balloon-expandable heart valve, and/or mechanically-expandable heart valve. The valve 110 in the illustrated embodiment can generally comprise a frame, or stent, 112, a leaflet structure 193 supported by the frame 112, and a sealing member or skirt 116 secured (e.g., sutured) to the outer surface of the leaflet structure 193. In certain embodiments, the valve 110 is configured to be implanted in the annulus of a native heart valve of a human, such as an aortic valve. However, the valve 110 can additionally or alternatively be adapted to be implanted in other native valves of the heart, or in various other vasculature, ducts, or orifices of the body, or in grafts, docking stents, docking stations, rings, etc. implanted in the body. The lower end 180, according to the illustrated orientation, of the valve 110 represents an inflow end, while the upper end 182, according to the illustrated orientation, of the valve 110 represents an outflow end.

The valve 110 and the frame 112 can be configured to be radially collapsible to a collapsed or crimped state or configuration for introduction into the body using a delivery catheter, and further can be configured to be radially expandable to an expanded state or configuration for implanting the valve at a desired location in the body (e.g., the native aortic valve). In certain embodiments, the frame 112 comprises a plastic, polymer, shape memory material, or metal expandable material that permits crimping of the valve 110 to a smaller profile for delivery and expansion of the valve. In certain implementations, an expansion device, such as the balloon of a balloon catheter or a tool for mechanical expansion, can be used to expand or help expand the valve. In certain embodiments, the valve 110 is a self-expanding valve, wherein the frame is made of a self-expanding material such as a shape memory material or metal (e.g., Nitinol). Self-expanding valves can be able to be crimped to a smaller profile and held in the crimped state with a restraining device, such as a sheath covering the valve. When the valve is positioned at or near the target site, the restraining device can be removed or retracted to allow the valve to self-expand to its expanded, functional size or to a deployed configuration.

The sealing portion or skirt 116 can comprise a single piece or multiple pieces or material (e.g., cloth, polymer, etc.) with opposite ends that are secured to each other to form the annular shape illustrated in FIG. 1 or extend around a circumference of the valve. In certain embodiments, the upper edge of the sealing portion or skirt 116 has an undulating shape that generally follows the shape of struts of the frame 112. In this manner, the upper edge portions of the sealing portion or skirt 116 can be tightly secured to respective struts with sutures 156. The sealing portion or skirt 116 can be placed on the outside of the frame 112 or on the inside of the frame 112 (as illustrated) and an upper edge portion of the sealing portion or skirt 116 can be wrapped around the upper surfaces of the frame struts and secured in place with sutures. The sutures 156 provide a durable attachment of the sealing portion or skirt 116 to the frame 112.

The leaflet structure 193 can comprise three leaflets (as illustrated in FIG. 1) in certain embodiments, which can be arranged to collapse in a tricuspid arrangement. Although a three-leaflet embodiment is illustrated, it should be understood that valve implants sutured according to embodiments disclosed herein can have any number of leaflets, such as, for example, two or four. The leaflets 193 can be formed from separate flaps of material or tissue or all three leaflets can be derived from a single material. The lower edge of leaflet structure 193 can have a variety of shapes. In certain embodiments, the lower edge of the leaflet structure 193 can have an undulating, curved, and/or scalloped shape that can be sutured to the frame 112. The leaflets 193 can be secured to one another at their adjacent sides to form commissures 184 of the leaflet structure, where the edges of the leaflets come together. The leaflet structure 193 can be secured to the frame 112 using any suitable techniques and/or mechanisms. For example, the commissures 184 of the leaflet structure can be aligned with the support posts 118 and secured thereto, e.g., using sutures, adhesive, clamping portions, crimping, and/or other attachment means. In certain implementations, the point of attachment of the leaflets 193 to the posts 118 can be reinforced, e.g., with bars comprising a more rigid material or stainless steel.

Figure 2:
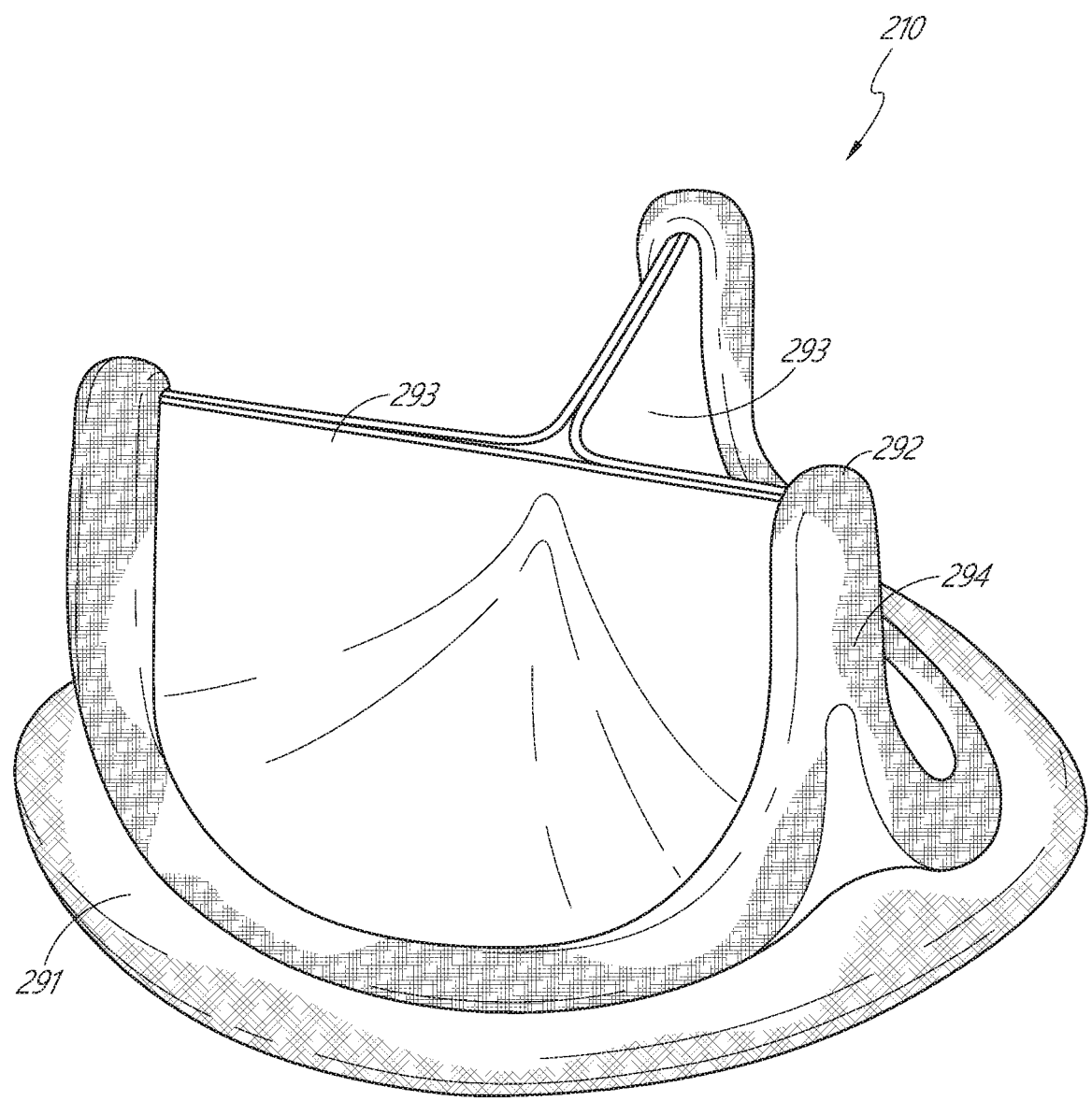
FIG. 2 illustrates a perspective view of an example of another prosthetic heart valve.

FIG. 2 illustrates a perspective view of a prosthetic human heart valve 210 in accordance with one or more embodiments. The heart valve 210 can include a peripheral sealing ring structure 291 configured to provide support for nesting the heart valve 210 in a heart valve cavity and/or resting upon, or attached to, an annulus or other structure of the heart. The valve 210 can further include a frame member 292, such as a metal frame, which can provide support for a plurality of flexible leaflets 293 and can define three upstanding commissure posts 294, wherein the leaflets 293 can be supported between the commissure posts 294. In certain implementations, as illustrated in FIG. 2, the sealing ring 291 can attach around the periphery of the frame member 294 at the inflow end of the valve 210, with the commissure posts 294 projecting in the outflow direction.

The leaflets 293 can be formed from separate flaps of material or tissue or all three leaflets can be derived from a single material. The leaflets 293 can be secured and supported both by the commissure posts 294, as well as along arcuate cusps of the frame member between the commissure posts.

Figure 3A:
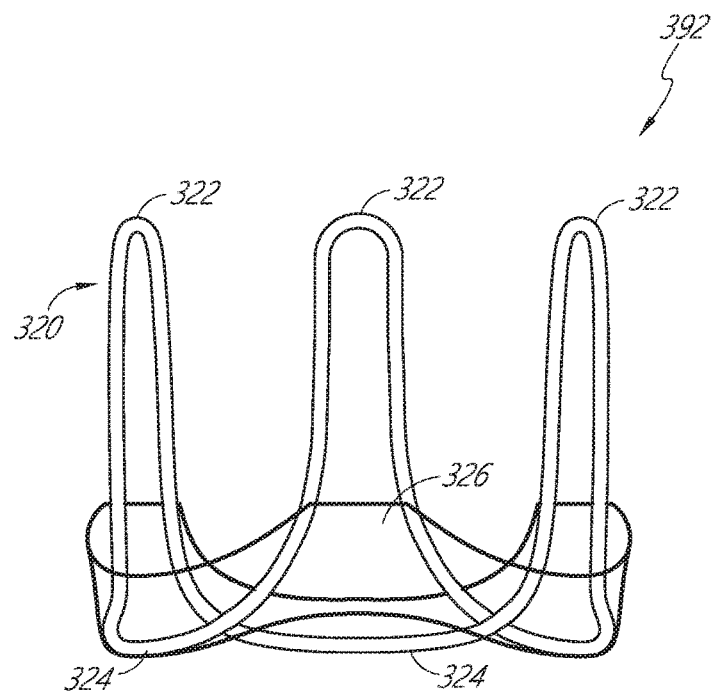
FIG. 3A illustrates a frame for a support stent for an example surgical valve.

FIG. 3A illustrates a frame 392 for a support stent for a surgical heart valve such as the valve 210 of FIG. 2. The frame 392 can include multiple cusps curved toward an axial inflow end alternating with multiple commissures 322 projecting toward an axial outflow end, the support stent 392 defining an undulating outflow edge. The support stent 392 can comprise a wireform 320 having three upstanding commissures 322 alternating with three cusps 324 which generally circumscribe a circumference. A stiffening band 326 can be disposed within or without the wireform 320. The inflow edge of the band 326 can conform or at least partially conform to the cusps 324 of the wireform 320 and can be curved in the outflow direction in between in the region of the wireform commissures 322, e.g., as illustrated in FIG. 3A. In some embodiments, the support stent 392 provides the supporting structure of a one-way prosthetic heart valve (e.g., valve 210) of FIG. 2.

Figure 3B:
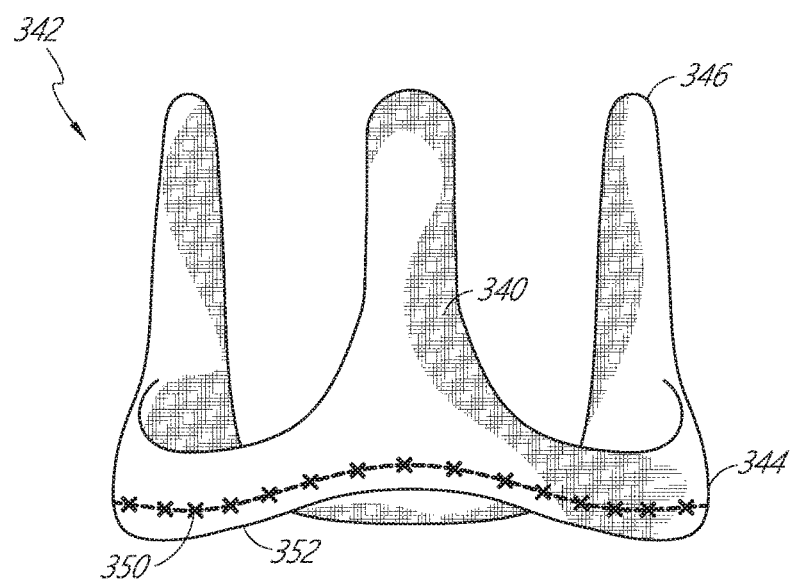
FIG. 3B illustrates the frame of FIG. 3A covered with fabric.

FIG. 3B illustrates the frame of FIG. 3A covered with fabric 340, wherein the fabric 340 can be sutured in one or more portions in order to secure the fabric 340 as a covering for the frame 392. The fabric-covered support stent 342 can be generally tubular and can include multiple cusps 344 curved toward an axial inflow end alternating with multiple commissures 346 projecting toward an axial outflow end. The support stent 342 can comprise an undulating outflow edge about which the fabric 340 is secured held. In certain embodiments, a seam 350 is sutured adjacent an inflow edge 352 that secures the fabric 340 about the support stent. The seam 350 is illustrated slightly axially above the inflow edge 352 for clarity, although it can be located directly at the inflow edge or even inside the support stent. In certain implementations, one or more seams can be located in other positions along the fabric. The sutures of the support stent 342 can be executed or added in multiple ways. Furthermore, although certain stitches are illustrated in FIG. 3B, the support stent 342 and/or valve implant 210 of FIG. 2 can comprise any type or number of stitches or sutures. For example, the support stent 342 and/or one or more other components of the associated implant device, can also have leaflets and/or other materials sutured thereto.

Figure 4:
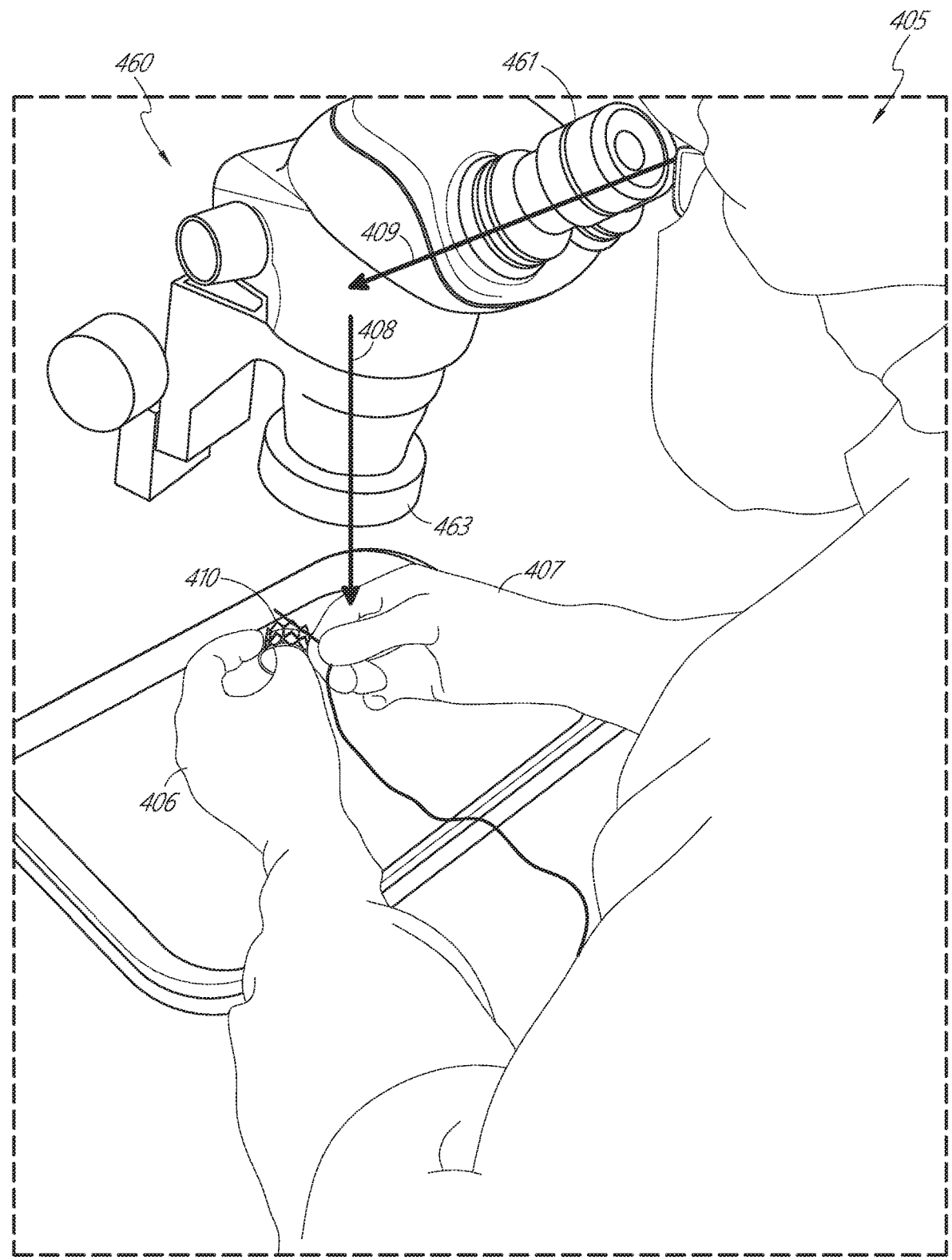
FIG. 4 illustrates an example of an operator performing operations on an implant device.

Suturing of prosthetic heart valve devices and/or other implant devices, such as those described above, can be performed in various ways. For example, certain handheld processes for suturing prosthetic human implant devices can be implemented in which an operator utilizes both hands for holding, securing, and/or suturing the implant device. FIG. 4 illustrates an operator 405 performing operations on a prosthetic human implant device 410. For example, the operator 405 can suture an outer wireframe of the device 410 to an inner skirt or cloth, as described above, where the implant device 410 is a transcatheter heart valve device. Alternatively, the implant device 410 can be a surgical valve device, or other type of implant device. The implant device 410 can be the same as or similar to one of the valves illustrated herein or can be a different type of valve or implant device.

As illustrated in the diagram of FIG. 4, in some processes, an operator 405 may need to utilize both of the operator's hands for executing relevant suturing operations. For example, a first hand 406 may be used to hold and/or secure the implant device 410, and a second hand 407 may be used to manually operate a suturing needle or the like.

In order for the operator 405 to effectively execute the relevant suturing operations on the implant device 410, it may be necessary or desirable for the view of the implant device 410 to be magnified or otherwise enhanced in some manner. For example, as illustrated, the operator may further utilize a magnification system 460, such as a microscope, which may comprise an eyepiece component 461 as well as one or more lenses and/or refractive elements 463. In certain embodiments, the magnification system 460 is designed such that the operator 405 may have a line of sight 409 at a first angle, wherein the magnification system 460 is configured to at least partially reflect light therein at a downward angle 408 to focus on a target focal plane below.

Figure 5:
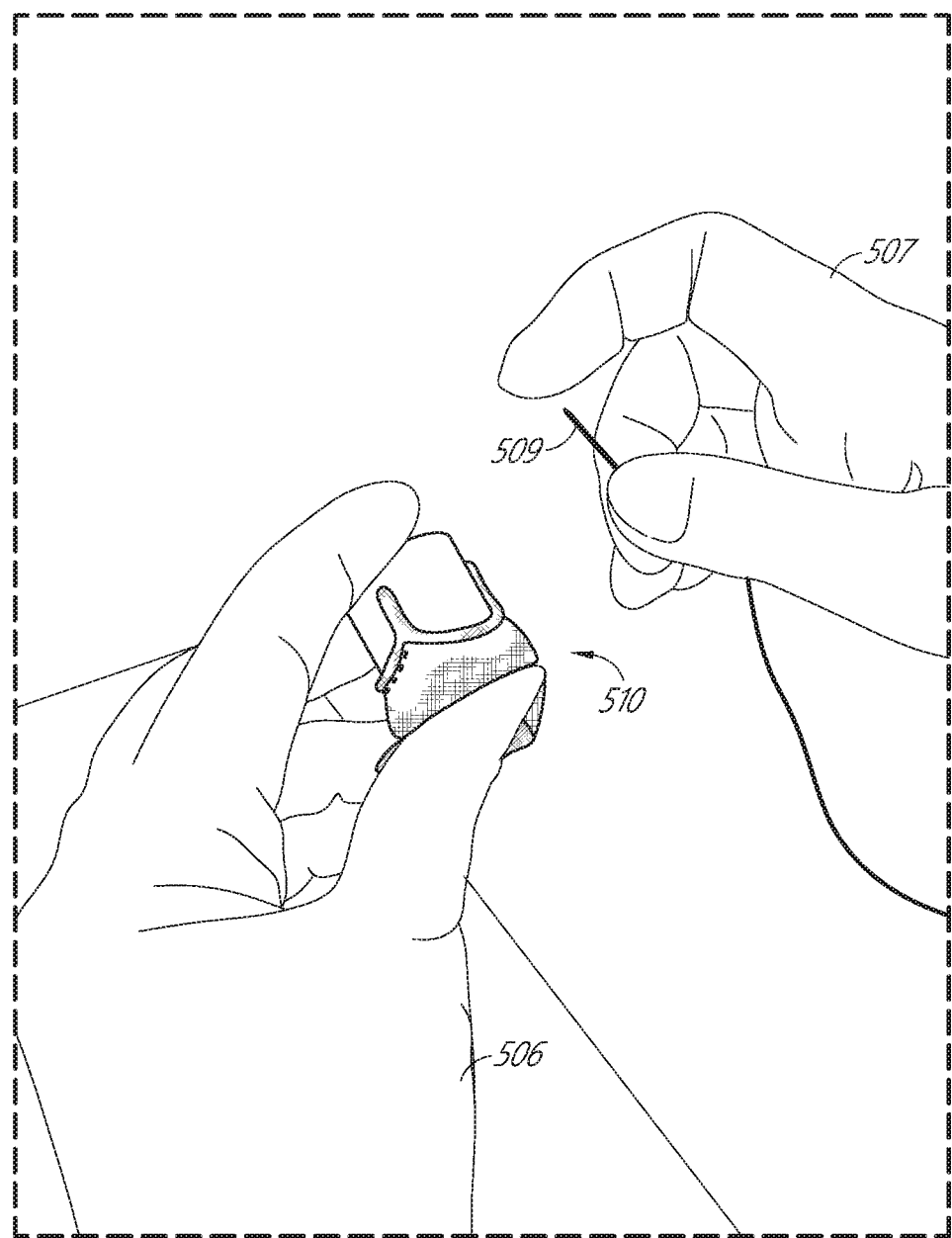
FIG. 5 illustrates a close-up view of a heart valve implant device being sutured using manual holding and suturing.

FIG. 5 illustrates a close-up view of a prosthetic human implant device being sutured using manual holding and suturing, as described above. As illustrated, for handheld suturing solutions, a first hand 506 may be required to hold the target implant device 510, while a second hand 507 may be required to manipulate the suturing needle 509, or the like. According to certain processes, the operator may be required to hold one or more hands in substantially constant focus of a microscope over prolonged periods of time. Furthermore, the operator may be required to squeeze, push, pull, or otherwise exert manual force on one or more portions of the target implant device 510 and/or suture needle 509.

Figure 6:
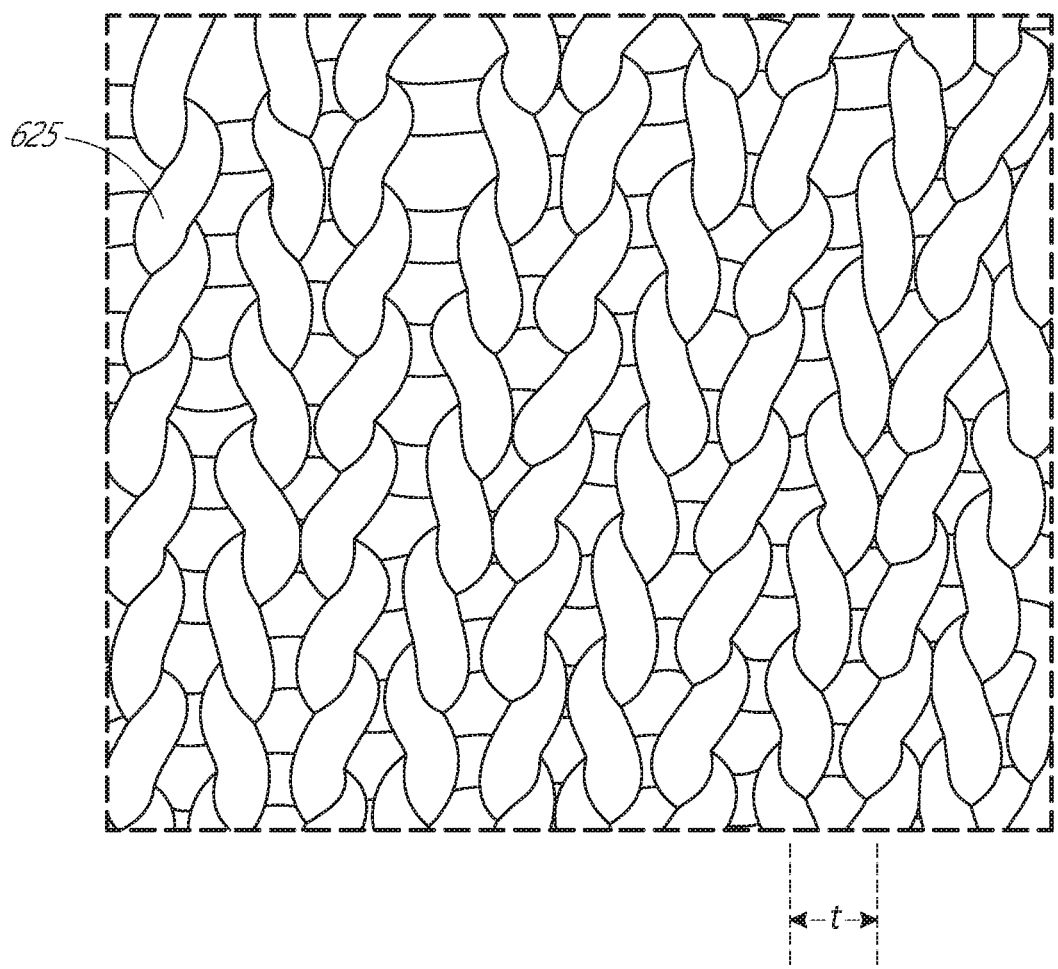
FIG. 6 illustrates a close-up view of a fabric that can be associated with an implant device.

FIG. 6 illustrates a close-up view of a fabric associated with an implant device according to one or more embodiments. Such fabrics may comprise woven strands forming ribs having relatively small gaps therebetween. For example, each rib in a fabric region to be sutured may have a thickness t of approximately 0.2 mm, or less. For certain processes, one may necessarily or desirably wish to position and sew such a fabric within one-rib accuracy. Thus, precise positioning and focusing of suturing components and targets is desirable.

To address issues identified above and to meet demand for heart valves and other implants, automation of the sewing operation could be beneficial in manufacturing, e.g., to cut down on touch time, human error, cost, etc.

Certain embodiments disclosed herein provide systems and processes for suturing components and/or devices (e.g., prosthetic implant devices) using multi-access systems and/or sewing systems for suturing implant devices. Such systems may be configured to articulate a component or device (e.g., an implant device such as a human prosthetic heart valve device, etc.) wherein the precise positioning of the component or device may allow for necessary or desirable suturing operations. Furthermore, the system may be further configured to reposition the component or device for a subsequent operation (e.g., a subsequent suture operation).

Suturing an implant device or heart valve can require suture accuracy within a millimeter, half a millimeter, or less, but a suture location may be easily missed between ribs or threads, especially when implementing dual-handheld suturing procedures. Embodiments of the present disclosure may facilitate improved precision and may help reduce or eliminate human error.

Positional accuracy may be improved with respect to embodiments of the present disclosure through the use of systems incorporating one or more cameras, sensors, articulation arms, automated fixtures, etc., and/or a combination of more than one of these for correctly positioning and identifying desired positions (e.g., suture positions, etc.), such as with respect to frame and skirt suturing for a transcatheter heart valve or other target device. Quality-controlled feedback for further improving quality for manufacturing can also be implemented, e.g., using sensors, imaging, and/or feedback mechanisms.

Embodiments disclosed herein provide for systems, devices, methods, etc. for executing one or more operations (e.g., suturing operations, review or inspection operations, and/or other operations) for prosthetic implant devices (e.g., prosthetic heart valves) for humans and/or other types of devices or components. The systems herein can be fully or mostly automated systems. The fully or mostly automated systems can include one or multiple automated fixtures. For example, a first automated fixture (which can be the same as or similar to the automated fixtures or automated suture fixtures described and illustrated herein) can be used to articulate and move an implant device to various desired positions for processing operations or steps (e.g., suturing, treatment, applications, etc.), while a second automated fixture or device could be used to perform the processing operations or steps at the various desired positions. For example, the second automated fixture can act similar to a sewing machine that moves a needle in and out (e.g., which can be done in a single plane and/or along a linear or curved path) to add the sutures to a target or implant device while the first automated fixture moves the target or implant device to the correct position to receive the desired suture in the correct location on the target or implant device. The automated sewing systems described herein can be programmed with a previously specified sewing pattern of an implant or heart valve. Suture tensioning management could also be used to maintain and use proper tensioning.

In certain implementations, a fully (or mostly) automated sewing process for one or multiple sewing operations can include two sub-systems or automated fixtures, in which one sub-system or automated fixture is configured to sew the pattern by translating movement of a needle while the other sub-system or automated fixture is coordinated or synchronized therewith and can utilize a multi-axis articulating arm (e.g., a five-axis robotic arm) to grip and move the target implant as desired for sewing. Within the sewing sub-system or automated fixture, various types of needles can be used. Also, the sewing sub-system or automated fixture can include a suture tensioning device configured to maintain the suture or thread attached to the needle in constant tension to avoid problems associated with slack in the suture or thread line (e.g., risk of entanglement, etc.). The implant holding sub-system or automated fixture can include a gripper that does not damage the implant and can be configured to accurately map the path of the implant holding device and an implant held thereby.

Figure 7:
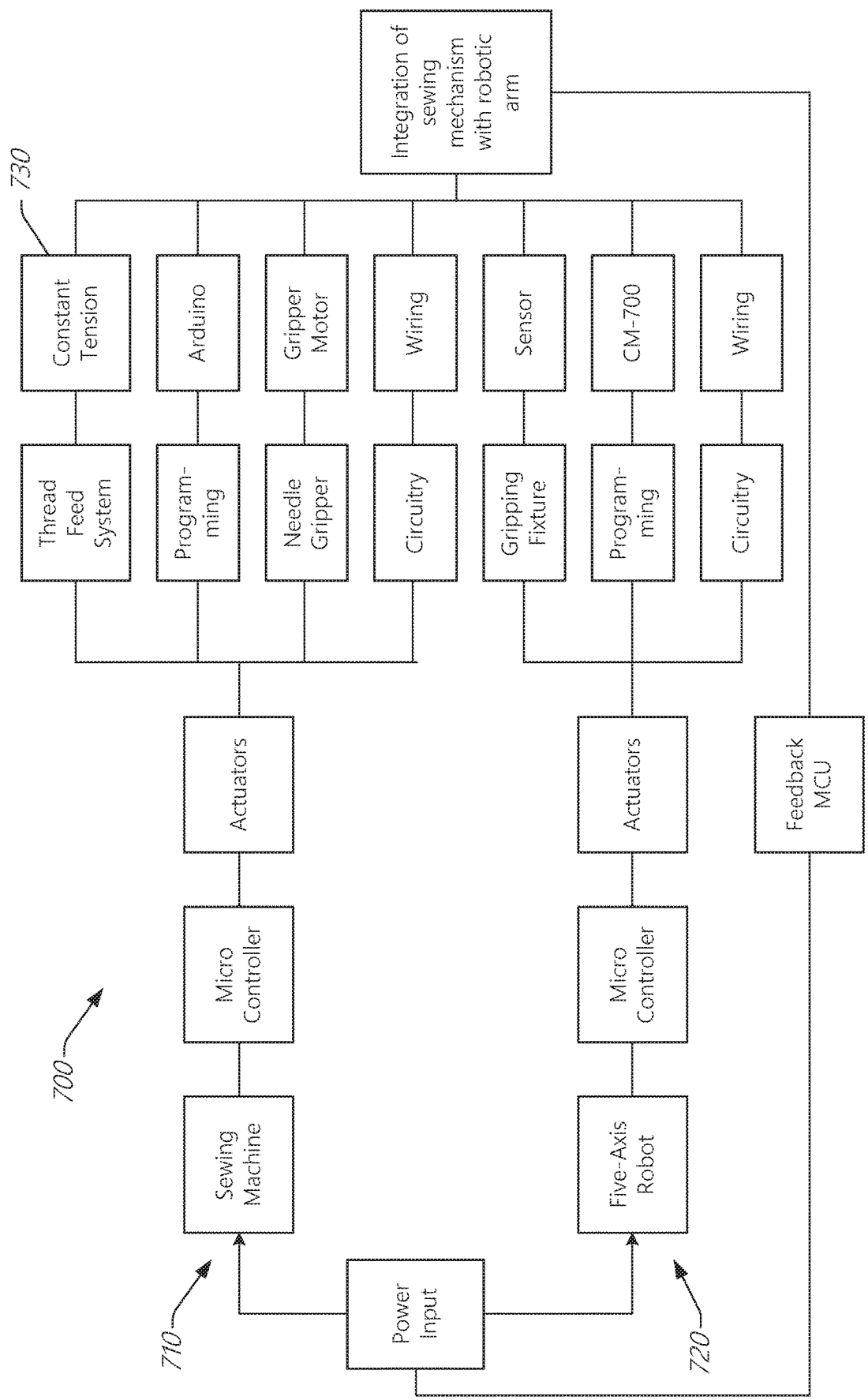
FIG. 7 illustrates a block diagram illustrating an example suturing system.
Figure 8A:
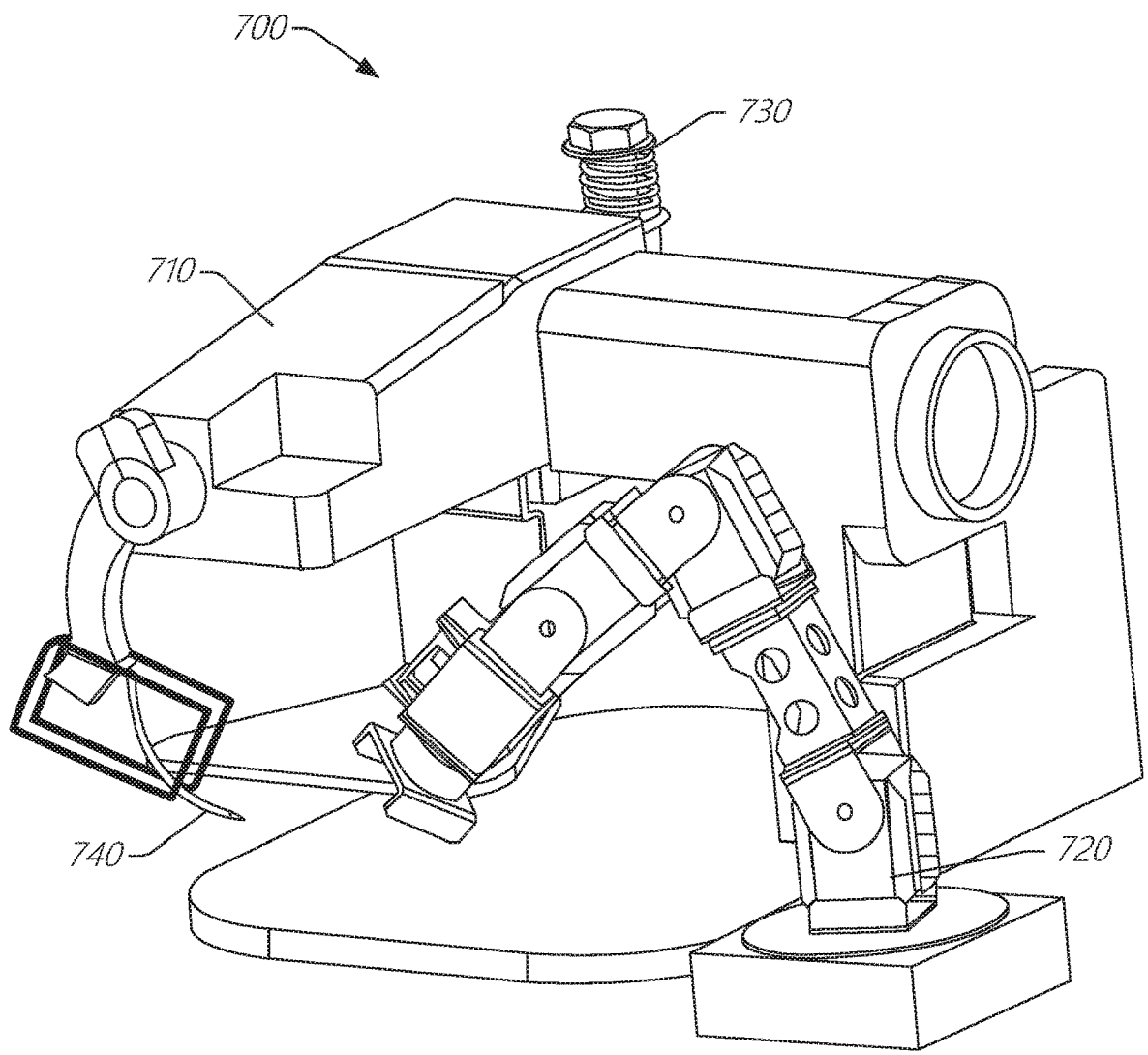
FIG. 8A illustrates a perspective view of an example suturing system.

FIG. 7 illustrates a block diagram of an exemplary suturing system 700, and FIG. 8A illustrates a perspective view of an exemplary version of the system 700. One or more components of the system 700 can be utilized for suturing heart valve devices or other implant devices, as described herein. The depiction of the system 700 in FIGS. 7 and 8A is meant to be illustrative and not limiting, so various components illustrated in FIGS. 7 and 8A can be omitted from the system 700 and other components not illustrated in FIGS. 7 and 8A can be added to the system 700. These are not drawn to scale and components can be various sizes. For example, in certain implementations, the needle is configured to be smaller than illustrated in FIG. 8A to make the suture line and punctures smaller and more precise.

As illustrated in FIG. 7, the system 700 can include one or more power inputs, a first automated fixture 710 (e.g., such as a sewing machine), a second automated fixture 720 (e.g., such as a multi axis robot or five axis robot), a feedback microcontroller unit (MCU), etc. In some embodiments, the power input is outlet power (e.g., of 110 volts) that can be configured to power one or both of the automated fixtures (e.g., one or both of an articulating arm and a sewing machine fixture), but other power inputs are also possible.

The first automated fixture 710 can include a controller (e.g., micro controller), one or more actuators, a thread or suture feed system, programming, a needle holder or needle gripper, circuitry, a constant tension component, arduino, a gripper motor, one or more sensors, wiring, and/or other components. The second automated fixture 720 can include a controller (e.g., micro controller), one or more actuators, a gripping fixture, programming, circuitry, one or more sensors, CM-700, wiring, and/or other components. The first automated fixture 710 and the second automated fixture 720 can be integrated and synchronized to perform sewing functions with the first automated fixture 710 (e.g., sewing machine) performing the suturing operations on a target implantable device held and moved into desired positions by the second automated fixture 720 (e.g., a multi-axis robotic arm).

In some embodiments, the system 700, for example one or more of the automated fixtures, includes one or more controllers (e.g., micro controllers) configured to direct one or more components of the automated fixtures and/or other components according to a suturing process. The controller(s) can comprise one or more hardware and/or software components designed to generate and/or provide fixture control signals (e.g., suture fixture control signals) and/or data associated with one or more steps of a suturing process. For example, the controller(s) can comprise a computing device including one or more processors, as well as one or more data storage devices or components, which can include volatile and/or nonvolatile data storage media. In certain embodiments, the data storage is configured to store process script data (e.g., suture process script data), which can comprise data indicating positioning of one or more components and/or fixtures of the system 700 for various steps and/or stages of the suturing process. A process comprising a plurality of steps can be represented at least in part by numeric or other data sets representing positioning information for one or more components of the automated fixtures and/or one or more additional components of the system 700 for each respective step or stage of the process. For example, a suturing process comprising a plurality of suturing steps can be represented at least in part by numeric or other data sets representing positioning information for one or more components and/or fixtures of the system of the system 700 for each respective step or stage of the suturing process.

The automated fixture 710 can comprise a needle 740. Various needles can be used. A non-corrosive curved needle comprising one or more of NiTi/Nitinol, Delrin, cobalt chromium, ABS plastic, PEEK plastic, strong plastic having a polycarbonate base can be used. The needle 740 can be curved into a semi-circular shape or a curved shape that does not form a complete circle. For example, in certain implementations, the needle has a curved shape forming an arc between 70 degrees and 220 degrees of rotation of a circle or between 100 degrees and 190 degrees.

The automated fixture 710 can comprise a needle gripper or needle gripping mechanism configured to hold the needle during sewing process. The needle gripper can comprise a drill chuck tool-holder, can use vacuum pressure, can comprise a mechanical gripper, etc. The automated fixture 710 can also comprise a tensioning device 730, such as system used to hold the spool of thread that is easily adjustable can keep the thread in constant tension. The tensioning device can comprise a spring system; a bolt and spring system; a bolt, nut, and spring system; a bobby tension meter; a PID controller; etc.

The automated fixture 720 can include a holder or holder assembly (e.g., a gripper or gripping fixture) configured to hold the target implant while sewing occurs. For example, a gripper can be a multi-prong gripper (e.g., a two or a three prong gripper) configured to hold the implant while sewing occurs. Optionally, the gripper can be an inside-bellow gripper, a pronged gripper, a 3-D printed gripper, a caged gripper, or another type of gripper. In some embodiments, a suture target holder assembly configured to hold or secure the suture target (e.g., the prosthetic implant device) can be similar to the target holder assembly illustrated in FIG. 10.

The automated fixture 720 can also include various sensors. For example, the fixture can include sensors to detect the position and rotation of the valve fixture during the sewing process and forces involved in the process. For example, the automated fixture 720 can also include a gripping force sensor, which can be configured to relay the force that the gripper exerts on the implant. The automated fixture 720 can also include a gyroscope sensor, which can be configured to measure the rotation of the second automated fixture or an articulation arm thereof. The automated fixture 720 can also include an accelerometer sensor, which can be configured to measure the position of the end effector of the automated fixture or an articulation arm thereof.

Figure 8B:
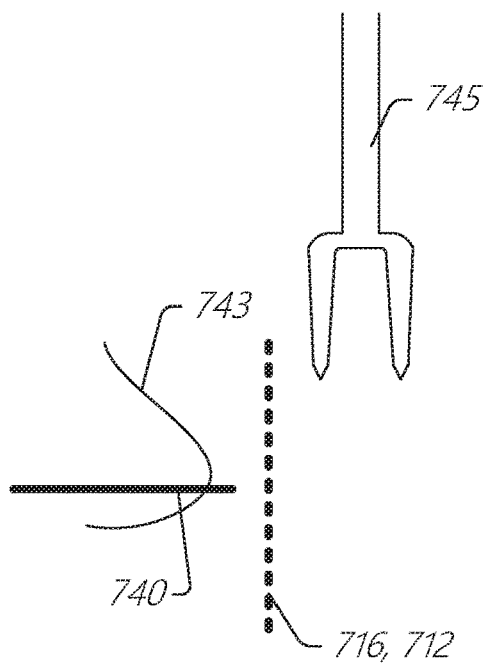
FIGS. 8B, 8C, 8D, 8E, 8F, 8G, and 8H illustrate an example process for suturing an implant device using the example suturing system of FIG. 8A.

While sewing operations with multiple sutures or threads are possible, in certain implementations, the automated fixture 720 is configured to perform a single suture or thread sewing operation to reduce the amount of suture or thread used and the volume of the implant. The automated fixture 710 can be configured as a modified hemming-like machine with a curved needle, thereby the process of transferring the needle after each pass through the material could be eliminated to allow a single thread operation. One way to do this is to use a machine that can sew or apply a suture or thread similar to a hemming machine or a blind stitch hemming machine, where the machine has been specially adapted and sized for use with an implant and coordinated with an automated fixture that automatically moves the implant as desired during suturing. Examples of procedures using such machines are illustrated in FIGS. 8B-8O. The curved needle can include an eyelet near the sharp or penetrating end of the needle (or between the end and another point along the needle, e.g., the middle of the needle) through which the suture or thread passes and the curved needle can direct the suture or thread into and then out of the material (e.g., a cover, seal, leaflet, or other material) being sewn to a stent or frame as the curved needle rotates. The automated fixture 720 can also include components that form and pull loops in the suture or thread to combine with other portions of the suture to form the stitching along the device. The automated fixture 710 is configured to move, rotate, etc. the target implant as the automated fixture 720 sews (e.g., moving the curved needle along a fixed path) to create a desired suture pattern. The movement of the target implant occurs in three dimensions. The automated fixtures can be programmed, coordinated, synchronized to work together to accomplish a variety of desired suture patterns on a variety of implants.

FIGS. 8B-8H illustrate an example process for forming a stitch in a target device or suture target having a fabric or other material 716 (e.g., the skirt 116 described with respect to FIG. 1) to be secured to a support structure 712 (e.g., the frame 112 described with respect to FIG. 1). The figures illustrate the process using a side cross-section view of the material or fabric 716 and the support structure 712 for simplicity and clarity. As illustrated in FIG. 8B, the process uses a needle 740 and a stitch looper 745 in an automated fixture (e.g., the automated fixture 710, an automated sewing fixture, etc.) wherein the movement of the needle 740 and the movement of the stitch looper are coordinated and/or locked together through the use of a common motor, common gears, or the like. The needle 740 can be a curved needle or a straight needle. The needle 740 holds a suture 743 which is passed through an eye of the needle 740. The stitch looper 745 includes two or more tines configured to hold a portion of the suture 743 and to form a loop with that portion of the suture 743 during the stitching process. The needle 740 can be configured to pass between the tines of the stitch looper 745 to form a stitch on the material or fabric 716.

Figure 8C:
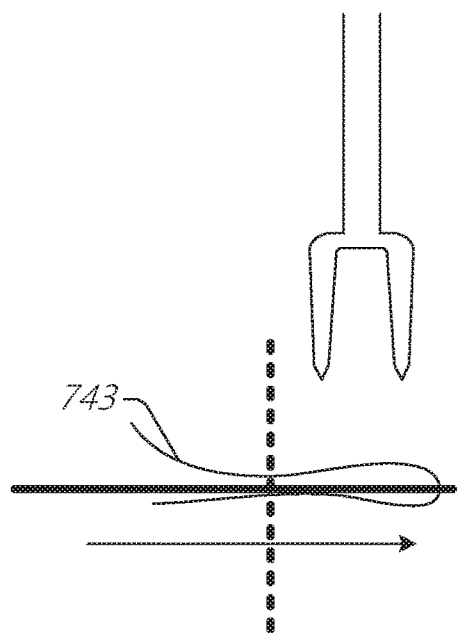
Figure 8D:
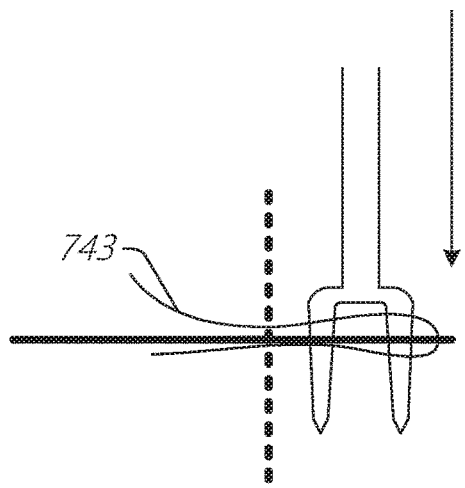
Figure 8E:
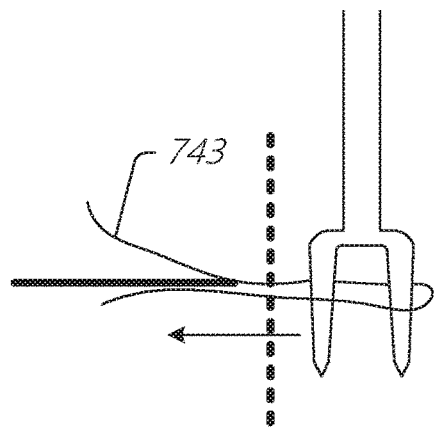
Figure 8F:
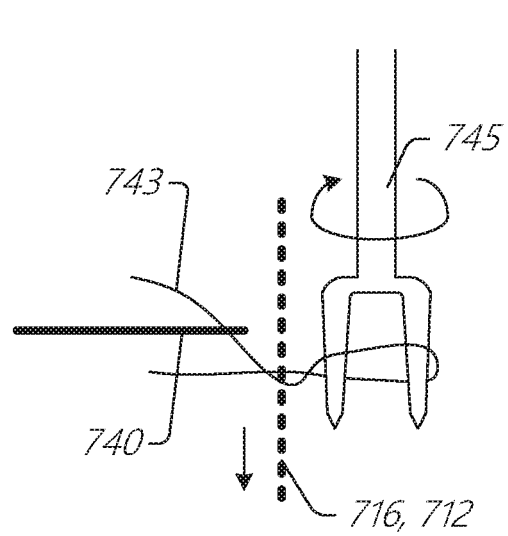
Figure 8G:
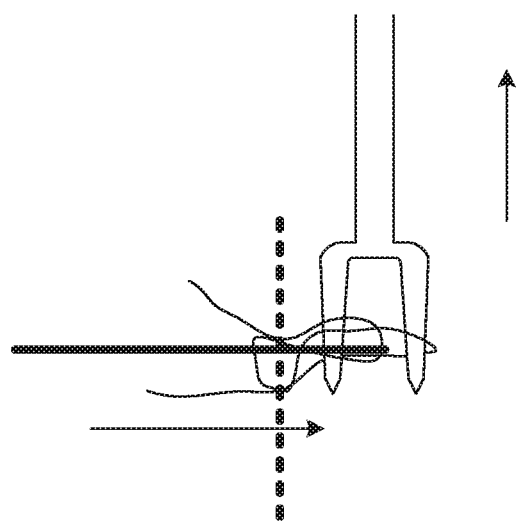
Figure 8H:
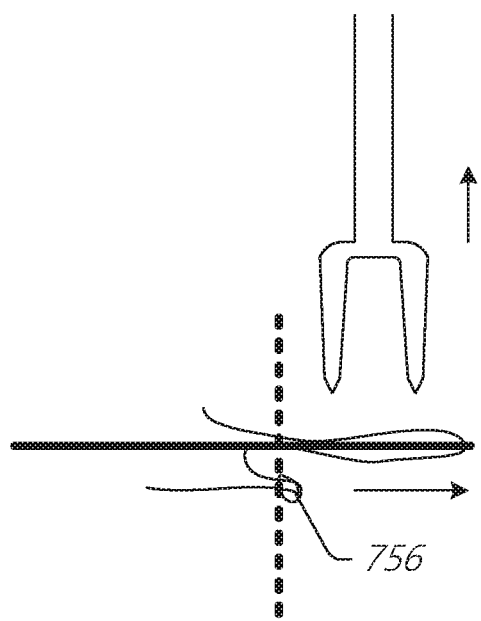

FIG. 8C illustrates the needle 740 being inserted through the skirt 116 so that the suture passes through the skirt at the insertion point. FIG. 8D illustrates the stitch looper 745 moving towards the needle 740 so that the stitch looper passes between a portion of the suture 743 and the needle 740. FIG. 8E illustrates the needle 740 being withdrawn through the same insertion point. The suture 743 remains wrapped around the stitch looper 745 to maintain a portion of the suture 743 on the opposite side of the material or fabric 716 as the withdrawn needle 740. FIG. 8F illustrates the stitch looper spinning to form a loop in the suture 743. In addition, the material or fabric 716 is moved relative to the needle 740 (e.g., by movement of an automated fixture or other means). FIG. 8G illustrates the needle 740 being inserted through the material or fabric 716 at a new insertion point due to the movement of the material or fabric 716 relative to the needle 740. The needle passes through the tines of the stitch looper 745 and the loop formed by the suture 743. As the stitch looper 745 is withdrawn (e.g., moved upward in the figure), the portion of the suture 743 held by the stitch looper 745 slides off of the tines of the stitch looper 745 so that the loop formed by the suture 743 tightens around the portion of the suture 743 held by the needle 740. FIG. 8H illustrates the stitch 756 formed by this process. The process repeats at the step illustrated in FIG. 8C for a stitch in a new location on the material 716.

FIGS. 8I-8O illustrate another example process for forming a stitch in a target device or suture target with a material or fabric 716 to be secured to a support structure 712. The process uses a curved needle 740 and a stitch looper 745 in an automated fixture (e.g., the automated fixture 710, an automated sewing fixture, etc.). The process is illustrated looking downward onto the material or fabric so that the curvature of the needle is not evident in the illustrations. However, the curvature of the needle 740 allows the needle 740 to be inserted through two points of the material or fabric 716 on either side of the support structure without needing to change the angle of the material or fabric 716 and/or without needing to pinch or bunch the material or fabric 716.

Figure 8I:
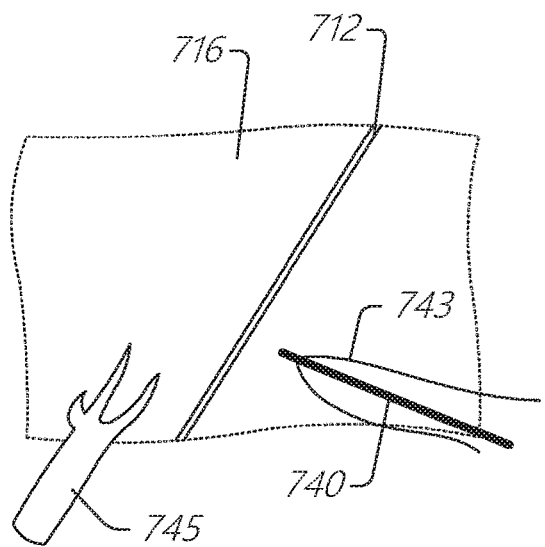
FIGS. 8I, 8J, 8K, 8L, 8M, 8N, and 8O illustrate another example process for suturing an implant device using the example suturing system of FIG. 8A.

FIG. 8I illustrates the curved needle 740 securing the suture 743 through an eye of the needle 740 at a distal end of the needle 740. The stitch looper 745 includes multiple tines configured to secure a portion of the suture 743 during the process. The stitch looper 745 is configured to hold a portion of the suture 743 while the needle 740 is withdrawn through the insertion points. The stitch looper 745 is also configured to form a loop in the suture 743 and to position the loop formed by the suture so that the needle 740 passes through the formed loop prior to creating new insertion points for the next stitch.

Figure 8J:
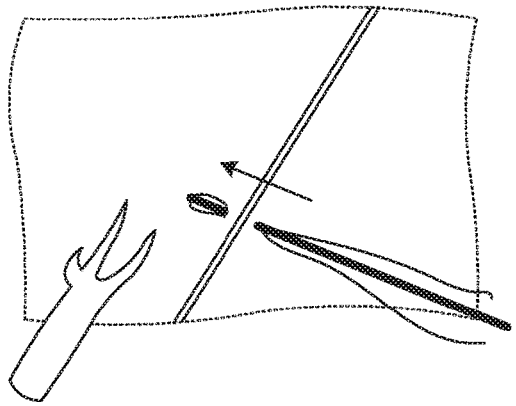
Figure 8K:
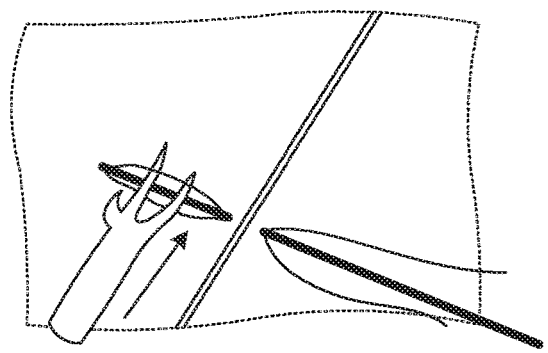
Figure 8L:
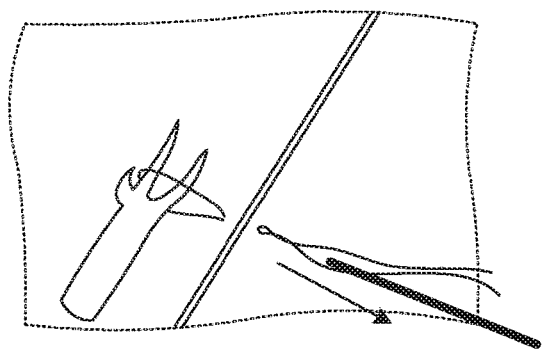
Figure 8M:
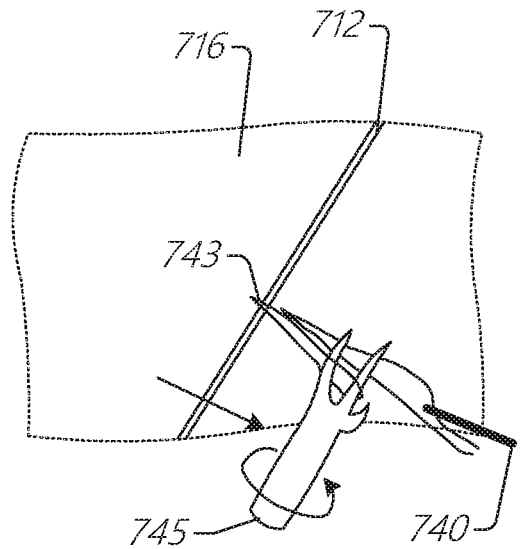
Figure 8N:
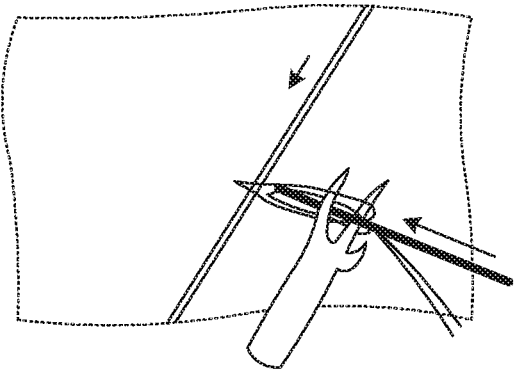
Figure 8O:
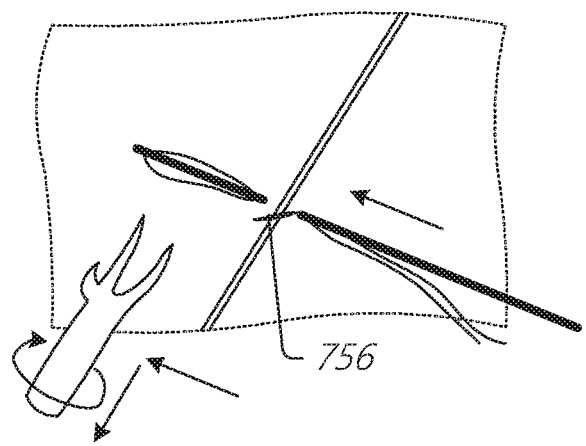

FIG. 8J illustrates the needle 740 forming two insertion points that pass through the material or fabric 716 under the support structure 712. The two insertion points are configured to be at complementary targeted locations to form a stitch that secures the material or fabric 716 to the support structure 712. FIG. 8K illustrates the stitch looper 745 moving toward the needle 740 to secure a portion of the suture. The stitch looper 745 passes between a portion of the suture 743 and the needle 740 to secure the portion of the suture 745. FIG. 8L illustrates the needle 740 being withdrawn through the same insertion points the needle 740 just created while the stitch looper 745 secures a portion of the suture 743 so that the portion of the suture 743 does not pass through those insertion points. FIG. 8M illustrates the stitch looper 745 moving toward the withdrawn needle in a way that also rotates the stitch looper 745. This movement produces a loop in the suture 743. FIG. 8N illustrates the fabric 716 being moved so that as the needle 740 is again being advanced, it will create two new insertion points. As the needle 740 advances, it passes through the loop formed by the suture 743 on the stitch looper 745. FIG. 8O illustrates the stitch looper 745 after it has been withdrawn and returned to its starting location. This movement of the stitch looper 745 causes the loop formed by the suture 743 to be removed from the stitch looper 745. In addition, advancement of the needle 740 through the two new insertion points pulls the loop formed by the suture 743 to tighten the loop around the suture 743, thereby forming the stitch 756. This process then repeats at the step illustrated in FIG. 8J to form additional stitches.

Advantageously, the processes described and illustrated in FIGS. 8B-8O can be used to form stitches in a fabric wherein the needle used to form the stitches is never released during the process.

With reference to FIGS. 7 and 8A, the system 700 can include a frame on which one or more automated fixtures (e.g., both automated fixture 710 and automated fixture 720, etc.) could each be mounted. In some embodiments, a frame that measure 16"×12"×12" can be used. The sides of the frame can be closed, or the sides of the frame can be open so that an operator can see the process happening and examine the fixture for any errors. The automated fixture 720 can be mounted to the front of the machine so that it could exit the sewing area, pick up the target implant and rotate back into the sewing area.

In certain embodiments, the automated suture fixture or fixtures comprise one or a plurality of motorized actuators (e.g., servo actuators) physically coupled to one another. By constructing the automated suture fixtures using one or a plurality of motor components (e.g., servo motor components), the system 700 may be relatively inexpensive and/or advantageously provide an enhanced range of motion, as well as multiple axes of rotation. In certain embodiments, one or more of the automated suture fixtures comprises a plurality of actuator devices (e.g., servo actuator devices) daisy-chained together and implemented using a software script to provide cooperative functionality for the purpose positioning the target implant device. For example, the actuator devices or servo actuator devices (e.g., servo motor devices) can be mounted, or configured to be mounted, horizontally or vertically or at an angle, and can be articulated in any direction.

In some embodiments, the second automated suture fixture or assembly comprises one or more components configured to articulate, operate, and/or position one or more motorized actuators to present a target device (e.g., a heart valve, implant, or other suture target), in a desirable or suitable position or presentation for convenient engagement or interaction therewith by another fixture executing at least part of a process (e.g., a suturing process). In certain embodiments, the automated suture fixture includes a plurality of motorized actuators that are mounted, attached, or connected to one another in a desirable configuration to provide a desirable range of motion for the automated fixture (e.g., automated suture fixture) for the purpose of articulating a target (e.g., a suture target) associated with or held by the automated fixture. In certain embodiments, a target holder component or assembly can be associated with, or connected to, one or more of the motorized actuators. The motorized actuators can each comprise one or more rotating or otherwise articulating members driven by a motor or the like. Examples of automated suture fixtures and associated components are illustrated in greater detail in FIGS. 7 and 8A and are described herein in greater detail in connection therewith.

In certain embodiments, the controller(s) provides one or more control signals for directing the positioning and/or operation of the fixtures (or motorized actuators of the fixtures) based on a positioning script, suture process script, and/or user input provided by an operator. For example, the system 700 (or a system 1000 described herein with reference to FIG. 9) can include a user input device (e.g., such as user input device 1010 illustrated in FIG. 9), which can be used by an operator to provide input initiating or directing the operation of the controller and/or automated suture fixture assembly. For example, user input device 1010 can comprise any suitable user input interface, such as a mechanism for user input in connection with a graphic user interface associated with an electronic display, wherein an operator can provide input through interaction with the interface. In some embodiments, the user input device comprises one or more physical switches, buttons, pedals, sensors, or the like, wherein a user may provide input through engagement of such mechanism(s). In some embodiments, the input can be provided using voice commands and/or voice recognition software. A signal or signals can be transmitted to advance from one step or stage of the present suturing operation to a subsequent step or stage, e.g., an input can be provided to the controller to advance the system through a script moving the automated fixture and target to each position in sequence. These can be coordinated such that the target is always moved to a position where the known, consistent path or fixed path of the needle will not contact a frame or metal of the implant to avoid damage to the needle and other problems.

The configuration of the automated suture fixture(s) can provide for a weight and/or size for the automated suture fixture(s) that is relatively small and convenient for use in applications designed to assist in the positioning and manipulation of relatively small devices, such as the prosthetic human implant device. The relatively small size of the system and automated fixture also allows for use in a more compact workspace like those often used for suturing prosthetic heart valve implants, e.g., the small size can fit and be used even on a relatively small desk or table, which allows for more efficient use of building and work areas. In certain embodiments, the individual actuator devices (e.g., the individual servo actuator devices) of the automated suture fixture(s) comprise brushless potentiostat and/or magnetic encoder devices. In certain embodiments the actuator devices are implemented using piezoelectric control with analog voltage signals. In certain embodiments, one or more components of the automated suture fixture(s) are controlled using pulse width modulation control signals, such as control signals spaced by between 0 to 2 μs, for example. In certain embodiments, multiple motor components (e.g., multiple servo motor components) of the automated suture fixture(s) share one or more common leads with a multiplex signal, such as a three-lead connection. In certain embodiments, the automated suture fixture(s) comprise four or five or more servo motor devices. Devices and fixtures disclosed herein can be remote-controllable or partially remote-controllable.

Figure 9:
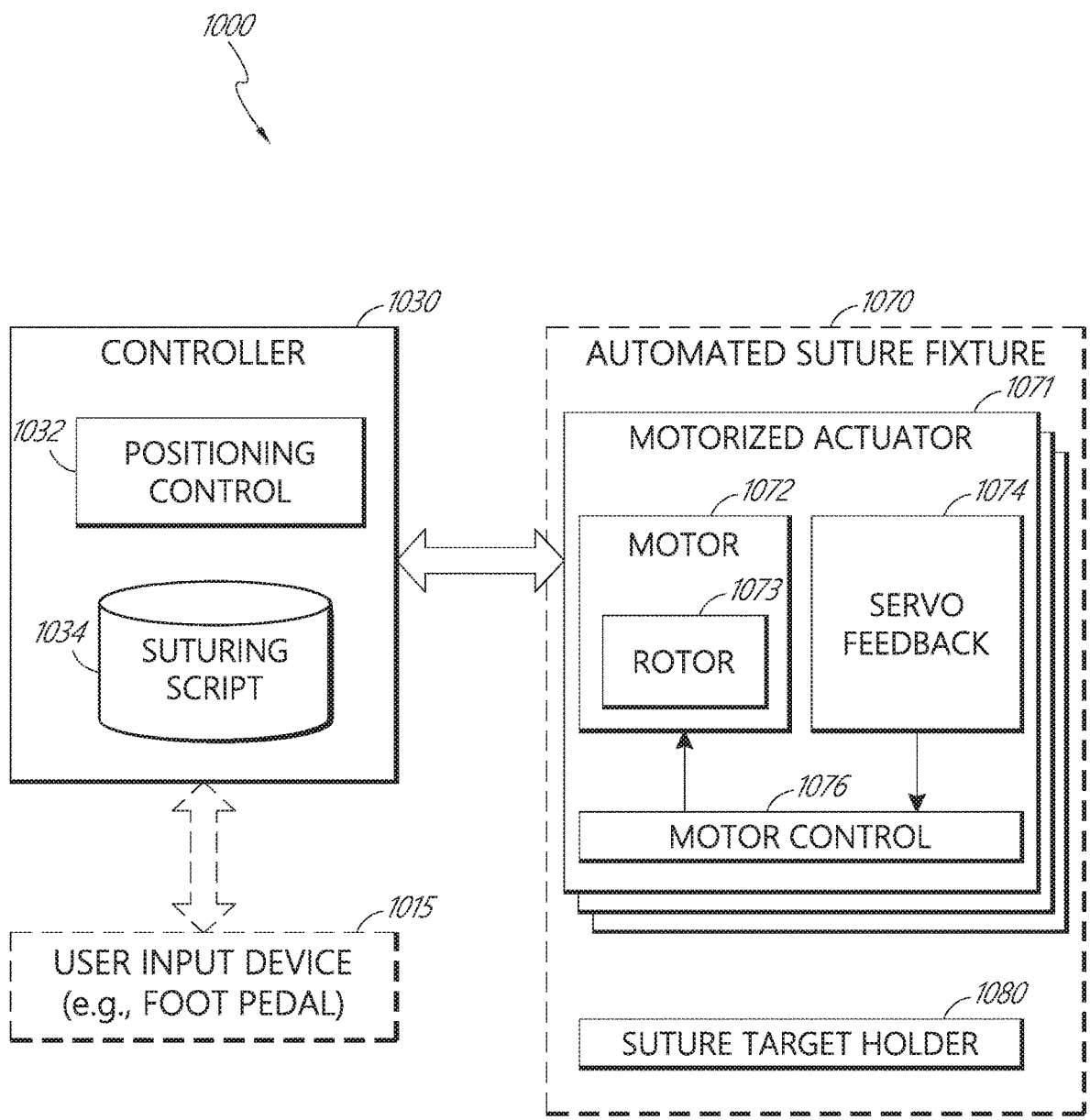
FIG. 9 illustrates a block diagram of an example control system for controlling an automated suture fixture.

Suture systems in accordance with the present disclosure can comprise one or more automated suture fixtures, e.g., an automated suture fixture 720 for articulating a suture target (e.g., prosthetic human heart valve implant) to a desired suture position or other process position. FIG. 9 illustrates a block diagram illustrating an exemplary control system 1000 for controlling an automated suture fixture 1070. The automated suture fixture 1070 (which can represent any or all of the automated fixtures described above) is configured to receive control signals from a controller module 1030. The controller module 1030 can comprise a combination of software and/or hardware components configured to generate control signals for at least partially directing the operation of the automated suture fixture 1070 and/or one or more components thereof.

In certain embodiments, the controller 1030 includes one or more processors and/or controller circuitry configured to access suturing script information 1034 or other script or program information maintained by the controller in data storage thereof, or otherwise accessed by the controller 1030. The controller 1034 can include positioning control circuitry 1032 designed to interpret suturing script information or other script or program information and generate control signals for controlling the automated suture fixture 1070 and/or another automated fixture based at least in part thereon.

The suturing script information 1034 or other script or program information can comprise sequential positioning information for one or more components of the automated suture fixture(s) 1070 with respect to one or more suturing processes or other processes that the controller 1030 is designed to implement. For example, in some embodiments, the positioning control circuitry 1032 is configured to provide position information for each step of a suturing process in sequence. The advancement from one position step to another can be directed by the controller 1030 based on a timer, or user input or other mechanism.

The automated suture fixture 1070 can include a plurality of motorized actuators 1071, which can be communicatively coupled to the controller 1030. In certain embodiments, the motorized actuators are coupled to one another in a daisy-chain configuration, wherein two or more of the motorized actuators are coupled or wired together in sequence.

Each of the motorized actuators 1071 can include a motor, such as a DC, AC, or brushless DC motor. The motor can be a servo motor. In certain embodiments, the motor 1072 is controlled using pulse-coded modulation (PCM), as directed by the motor control circuitry 1076. For example, the motor control circuitry 1076 can apply a pulse application for a certain period of time, wherein the angular positioning of a rotor component 1073 is determined at least in part by the length of the pulses. The amount of power applied to the motor 1072 can be proportional to the rotational distance of the rotor 1073.

In certain embodiments, the motorized actuators are servo actuator devices including one or more servo feedback component(s) 1074, such as a position sensor (e.g., a digital encoder, magnetic encoder, laser(s), etc.). Use of servo feedback component(s) 1074 may be desirable in order to achieve a desirable level of confidence that the motorized actuators 1071 are positioned as directed by the controller 1030 with an acceptable degree of accuracy. The servo feedback component(s) 1074 can provide an analog signal to the motor control circuitry 1076 indicating a position and/or speed of the rotor 1073, which may advantageously allow for relatively precise control of position for faster achievement of a stable and accurate rotor position. Relatively accurate positioning of an implant device may be necessary or desirable due at least in part to the dimensions of the material or cloth of a heart valve or other implant device that is sutured in an implant suturing operation using the automated suture fixture 1070. For example, the fabric or other material being sutured can comprise woven strands forming ribs having relatively small gaps therebetween. In certain embodiments, the automated suture fixture 1070 can be configured to articulate a suture target prosthetic human implant device within 0.2 mm accuracy, or less. Although servo motor devices and components are described, in some embodiments, one or more motorized actuators can comprise stepper motors, or other types of motor subsystems.

The motorized actuators 1071 can further comprise motor control circuitry 1076, which can drive the motor 1072 according to the control signals received from the controller 1030. In certain embodiments, the motor 1072, in combination with the servo feedback mechanism 1074 and/or motor control circuitry 1076, can advantageously be configured to retain the rotor 1073 and/or attached support member in a set position for desired periods of time. The motor 1072 can provide relatively smooth commutation and/or accurate positioning of the associated rotor 1073. The motor 1072 can be relatively powerful relative to its size and may draw power proportional to the mechanical load present on the rotor 1073 and/or associated support member.

In some embodiments, the servo feedback component 1074 comprises a potentiometer that is connected to the rotor 1073, which can be the output device of the motorized actuator 1071. The rotor 1073 can link to the potentiometer and control circuitry 1076, wherein the potentiometer, coupled with signals from the control circuitry, controls the angle of the rotor 1073 (and associated support member) across a rotational range, such as between 0°-180°, or further. In certain embodiments, the rotational range of the rotor 1073 is restricted by one or more mechanical stops, which can be built into associated gear mechanism(s). The potentiometer (or other servo mechanism, such as an internal rotary encoder) can allow the control circuitry 1076 to monitor the current angle of the motor or rotor. When the rotor 1073 is at the correct angle, the motor 1072 can idle until the next positioning signal is received from the controller 1030.

The automated suture fixture 1070 can further include a suture target holder device or assembly 1080 (while called a suture target holder or assembly herein, this can be another type of target holder device, gripper, or assembly to hold target devices or components for other procedures). The suture target holder 1080 can be physically coupled to one of the motorized actuators 1071, such as to distal extension arm actuator device of the plurality of actuators. The suture target holder 1080 can be configured to hold or have mounted thereto a prosthetic heart valve device, or other prosthetic human implant device, which is desired to be sutured. The suture target holder 1080 can have any suitable or desirable shape, configuration and/or dimensions and can be configured to hold or secure a target device or implant device in a variety of different ways. An example embodiment of suture target holder device or assembly is described below in connection with FIG. 10. However, it should be understood that such an embodiment is provided merely as an example, and other types of suture target holders can be implemented in the disclosed systems.

Figure 10:
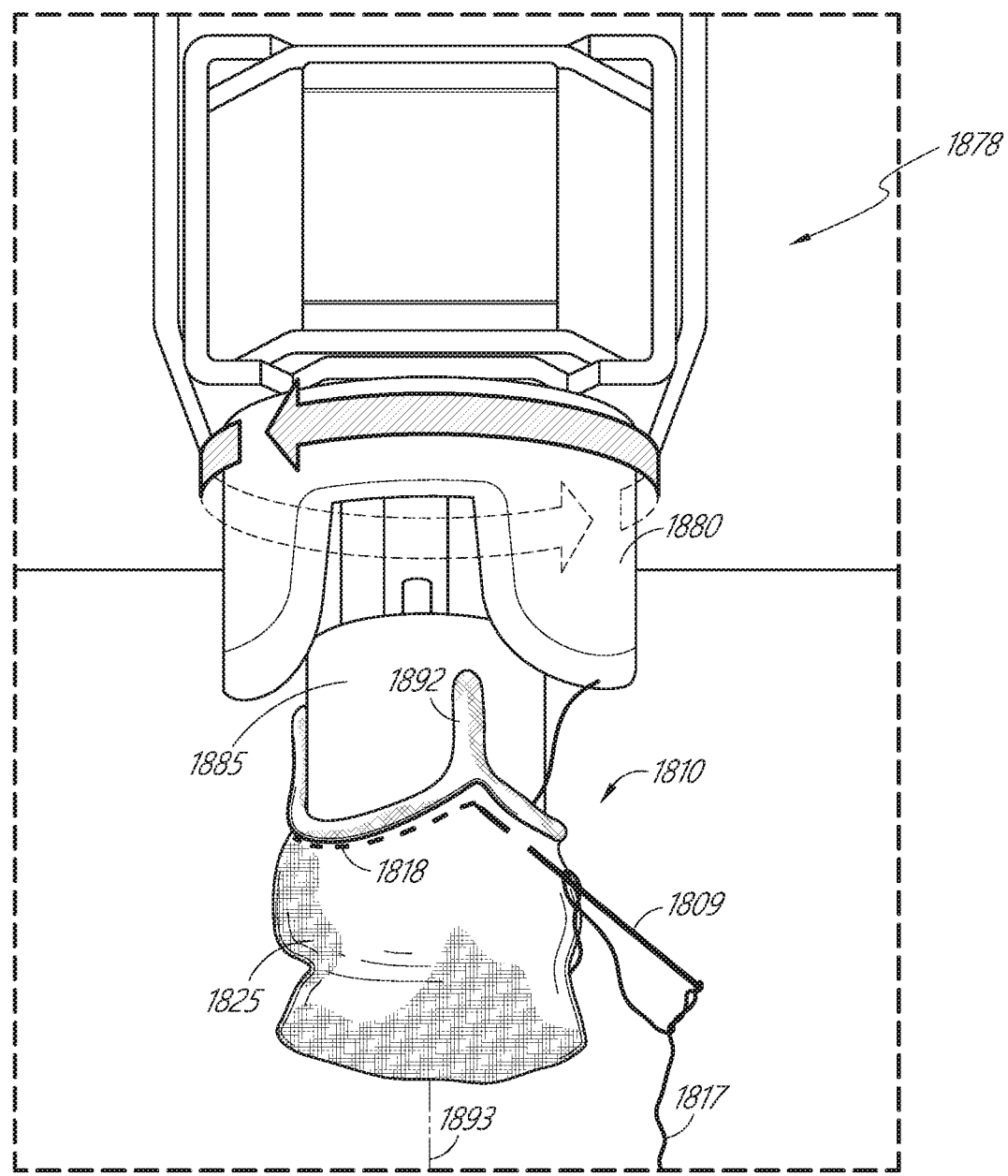
FIG. 10 illustrates an example distal articulation arm of an automated suture fixture coupled to a holder component.

FIG. 10 illustrates an articulation arm 1878 and/or one or more actuators coupled to an exemplary holder component 1880. In certain embodiments, a holder component 1880 is fixed or secured to the distal articulation arm 1878 or end actuator of an automated suture fixture for the purpose of providing an interface for securing an implant device or other target form or device. The holder component or assembly 1880 can be designed or configured to hold or secure an implant device or other target device, or portion thereof, for the purpose of allowing suturing thereof according to any process or embodiment disclosed herein. The holder component 1880 can be configured to secure or otherwise include a cylinder form 1885, which can be sized or dimensioned to have pulled thereover the target device or implant (e.g., a fabric-covered support stent for a surgical valve implant device 1818). For example, the valve implant device 1818 can comprise a plurality of commissure post portions 1892, as illustrated, which can be positioned such that they are oriented in a direction towards the holder component 1880, such that a seam 1818 can be stitched above what will ultimately represent an inflow edge of the implant device 1818. The cylindrical form or component 1885 can be designed in a similar manner to a handheld implant device holder, which can be used in certain embodiments in executing suturing procedures without the assistance of the articulation arm 1878 and associated components. The cloth 1825 can be disposed about a rigid wireframe structure, wherein the seam of stitches 1818 is executed in order to substantially cover the wireframe with the cloth 1825. The seam 1818 can secure the cloth 1825 about a stiffening band, as illustrated in FIG. 3A and described.

The holder component 1880 can be designed for a particular application, such as for a transcatheter heart valve suturing application, or a surgical heart valve suturing operation, or other implant suturing procedure. The valves can be for animal (e.g., for human) use. Although a surgical valve configuration is illustrated in FIG. 10, it should be understood that the holder device 1880 and/or other components of FIG. 10 can be designed or configured to support suturing processes and/or other processes for a transcatheter heart valve or other valve or other device. For example, although the diagram of FIG. 10 illustrates a cylindrical form 1885 designed to hold the implant device 1818 in a desired position, such cylindrical form may not be necessary with respect to a transcatheter heart valve. For example, in place of the cylindrical form 1885, the holder 1880 can instead be configured to secure a rigid cylindrical wireframe of a transcatheter heart valve, an embodiment of which is illustrated and described above in connection with FIG. 1.

The specific type of holder that is utilized for a procedure or application (e.g., for a suture assist application) can be determined on a process-by-process basis. That is, specific adapters may be suitable or desirable for each of separate operations or procedures, or for separate types of valves or other targets. In certain embodiments, a single suturing procedure of an implant device can involve use of multiple different types of holder devices.

A suturing procedure can be performed after a suture system has been programmed with a certain procedure, program, or script. One or more computer components, such as one or more processors and/or memory devices, can be utilized to store and execute a procedure-directing script or program, such that a procedure script or program may be played back for an operator on-demand.

The procedure can include loading a suturing process script or program, which can be pre-programmed. The desired script or program can be loaded in various ways, e.g., by providing input to the system or a computer of the system to load the desired script or program from storage or memory The procedure can involve triggering the positioning of an automated suture fixture (or automated fixture) and/or executing a suturing operation or other operation or step.

Once the suturing operation or other operation or step has been executed, if the relevant suturing operation or other operation or step represents a final operation or step of the suturing procedure or other procedure, the process can end. However, if additional steps of the suturing operation or procedure or other operation or procedure remain, the process can repeat the triggering, positioning, or executing steps where a subsequent step of the suturing process or procedure can be triggered, such that the process 1700 can involve completion of subsequent step(s).

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events can be performed concurrently rather than sequentially. For example, multi-threaded processing, interrupt processing, and/or multiple processors or processor cores could be used.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments do include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

The methods described herein include steps that are indicative of one or more embodiments of the presented method. Other steps and methods may be conceived that are equivalent in function, logic, or effect to one or more steps, or portions thereof, of the procedures or methods herein. Additionally, the order in which steps of a particular method occurs may or may not strictly adhere to the order of the corresponding steps described. Components, features, steps, etc. described with respect to one embodiment herein can be combined or included in other embodiments described elsewhere herein.

Components, aspects, features, etc. of the systems, assemblies, devices, apparatuses, methods, etc. described herein can be implemented in hardware, software, or a combination of both. Where components, aspects, features, etc. of the systems, assemblies, devices, apparatuses, methods, etc. described herein are implemented in software, the software can be stored in an executable format on one or more non-transitory machine-readable mediums. Further, the software and related steps of the methods described above can be implemented in software as a set of data and instructions. A machine-readable medium includes any mechanism that provides (e.g., stores and/or transports) information in a form readable by a machine (e.g., a computer). For example, a machine-readable medium includes read only memory (ROM); random access memory (RAM); magnetic disk storage media; optical storage media; flash memory devices; DVD's, electrical, optical, acoustical or other forms of propagated signals (e.g., carrier waves, infrared signals, digital signals, EPROMs, EEPROMs, FLASH, magnetic or optical cards, or any type of media suitable for storing electronic instructions. Information representing the units, systems, and/or methods stored on the machine-readable medium can be used in the process of creating the units, systems, and/or methods described herein. Hardware used to implement the invention can include integrated circuits, microprocessors, FPGAs, digital signal controllers, stream processors, and/or other components.

What is claimed is:

1. A method of suturing an implant device, the method comprising:
   disposing the implant device on a holder component of a first automated fixture;
   directing the first automated fixture to position the implant device in a first position;
   directing a second automated fixture to execute a first stitch on the implant device by passing a curved needle into and out of a material being sutured to the implant device;
   directing the first automated fixture to position the implant device in a second position; and
   directing the second automated fixture to execute a second stitch on the implant device by passing the curved needle into and out of the material being sutured to the implant device, the second automated fixture including a stitch looper that moves in coordination with the curved needle to form the first stitch and the second stitch;
   wherein the stitch looper includes two or more tines to secure a portion of the suture as the curved needle is withdrawn through insertion points formed during formation of the first stitch.

2. The method of claim 1, wherein the implant device is a prosthetic heart valve.

3. The method of claim 1, further comprising directing the first automated fixture to circumferentially rotate the implant device in place.

4. The method of claim 1, further comprising loading a pre-programmed suturing procedure script using one or more processors configured to at least partially control the first automated fixture and the second automated fixture.

5. The method of claim 1, wherein the second automated fixture uses the curved needle to execute the first stitch such that the first stitch is a single suture stitch.

6. The method of claim 1, wherein the curved needle passes into and out of the material along a fixed path of the curved needle.

7. The method of claim 1, wherein the stitch looper is configured to rotate to form a loop with the portion of the suture to form the first stitch.

8. The method of claim 7, wherein the curved needle passes through the loop formed by the stitch looper to form the first stitch.

9. The method of claim 1, wherein the curved needle passes through a fabric of the implant device at two different locations for each of the first stitch and the second stitch.

10. A suturing system comprising:
    a first automated fixture comprising a plurality of motorized actuator devices and a suture target holder, the first automated fixture being configured to rotate the target suture device when mounted to the suture target holder;
    a second automated fixture comprising a curved needle that is configured to move the curved needle in a fixed path and a stitch looper having a plurality of tines that is configured to secure a portion of a suture and to form a loop using the portion of the suture as the curved needle moves in the fixed path; and
    wherein the first automated fixture and the second automated fixture are arranged relative to each other and configured such that the first automated fixture can move the target suture device in three dimensions to position the suture device in the path of the curved needle to implement a predetermined suturing pattern on the target suture device.

11. The suturing system of claim 10, wherein the target suture device is a heart valve.

12. The suturing system of claim 10, wherein the first automated fixture comprises a first controller configured to direct the first automated fixture how to position the target suture device.

13. The suturing system of claim 10, wherein the second automated fixture comprises a second controller configured to direct the second automated fixture when to move the curved needle to implement the suturing pattern.

14. The suturing system of claim 10, wherein the second automated fixture includes a tensioning device that can keep a suture in a state of constant tension when implementing the suturing pattern.

15. The suturing system of claim 10, wherein the first automated fixture is configured to move the target suture device in at least four directions.

16. The suturing system of claim 10, wherein the first automated fixture comprises an articulation arm.

17. The suturing system of claim 10, wherein the second automated fixture is configured such that the curved needle is used to implement the suturing pattern as a single suture stitching.

18. The suturing system of claim 10, wherein movement of the curved needle is locked to movement of the stitch looper.

19. The suturing system of claim 10, wherein the stitch looper moves along a second fixed path that includes rotation of the stitch looper to form the loop using the portion of the suture.

* * * * *